United States Patent [19]

Meyers et al.

[11] Patent Number: 4,828,835

[45] Date of Patent: May 9, 1989

[54] EMULSIFIABLE POLYMER CONCENTRATE

[75] Inventors: Paul A. Meyers, Dublin, Calif.; Linneaus C. Dorman, Midland, Mich.

[73] Assignee: The Dow Chemical Company, Midland, Mich.

[21] Appl. No.: 871,002

[22] Filed: Jun. 5, 1986

[51] Int. Cl.$^4$ ............................................. A01N 25/08
[52] U.S. Cl. ...................................... 424/409; 424/78; 424/405; 514/938; 514/746; 514/760
[58] Field of Search .......................... 424/78, 405, 409; 514/746, 938, 760

[56] References Cited

U.S. PATENT DOCUMENTS

| | | | |
|---|---|---|---|
| 2,441,553 | 5/1948 | Britton | 167/39 |
| 2,502,244 | 3/1950 | Carter | 514/746 |
| 2,966,440 | 12/1960 | Gerolt et al. | 167/42 |
| 4,303,642 | 12/1981 | Kangas | 424/78 |
| 4,460,572 | 7/1984 | Derby et al. | 424/78 |

FOREIGN PATENT DOCUMENTS 1494814 12/1977 United Kingdom .

*Primary Examiner*—John S. Maples
*Attorney, Agent, or Firm*—S. Preston Jones; Ronald G. Brookens

[57] ABSTRACT

A storage stable, water emulsifiable, substantially non-aqueous liquid or low melting solid concentrate adapted for on-site preparation of an aqueous emulsion of an agricultural chemical, consisting essentially of a solution, in (a) a liquid hydrophobic agricultural chemical having biocidal activity, of
(b) a solid hydrophobic polymer, in an amount effective to achieve sustained release of (a), and
(c) an emulsifying agent, in an amount effective to form a stable oil-in-water emulsion when the concentrate is mixed with water.

12 Claims, No Drawings

EMULSIFIABLE POLYMER CONCENTRATE

BACKGROUND OF THE INVENTION

This invention relates to concentrates of agricultural chemicals suitable for the formation of oil-in-water emulsions of a water insoluble biocide therein, more particularly to a stable, emulsifiable concentrate suitable for the controlled delivery of an agricultural biocide after being formed into an aqueous emulsion, and to processes for the manufacture and use thereof.

DESCRIPTION OF THE PRIOR ART

U.S. Pat. No. 4,282,209 is directed to a process for the preparation of controlled release particles of the insecticide methomyl. Initially, methomyl and a polymer, such as polystyrene are dissolved in an organic solvent. The object of the patent is to form particles containing insecticide and the polymer.

U.S. Pat. 4,177,177 discloses the direct emulsification of polymers using oil-in-water emulsifiers, polystyrene polymers, a water immiscible solvent which is later removed by evaporation, and extensive mechanical mixing requiring sophisticated equipment, such as is available in a factory or a laboratory, is required.

U.S. Pat. No. 4,336,173 discloses the preparation of an aqueous emulsion or dispersion of a partly water soluble material with an option to further prepare a polymer dispersion when the dispersed material is a polymerizable monomer.

U.S. Pat. No. 3,167,661 and U.K. Specification No. 1,494,814 are also directed to the preparation of state of the art types of emulsions.

U.K. Patent No. 1,494,815 discloses the preparation of concentrated resin emulsions for the controlled release and delivery of herbicides wherein such resins are filmforming and hydrophilic, derived from polyurethanes, polyesters or vinylpolymers which are combined with one or more polyoxyethylene chains.

U.S. Pat. No. 3,156,661 discloses the preparation of latex products comprising dispersed resinous polymeric materials and water composed "predominantly of monomer units such as styrene", wherein the particles dispersed in the aqueous phase contain an insecticide.

In copending U.S. patent application Ser. No. 871,001 filed on June 5, 1986 concurrently with the present application, a storage stable, water emulsifiable, substantially anhydrous, liquid concentrate adapted for on-site preparation of an aqueous emulsion of an agricultural chemical was disclosed consisting essentially of a solution of (a) a hydrophobic agricultural chemical having biocidal activity, (b) a solid hydrophobic polymer, in an amount effective to achieve sustained release of (a), (c) a water immiscible organic solvent, and (d) an emulsifying agent, in an amount effective to form a stable oil-in-water emulsion when the concentrate is mixed with water.

It has been recognized for some that particulate biocides can be used effectively to control weeds, insects and other pests while, by controlling the rate of release of the biocide, minimizing the undesirable effects of these generally toxic chemicals. However, this basic process is limited in many regards and may require a variety of relatively expensive techniques which are difficult to employ. For example, techniques such as microencapsulation are quite expensive and can lead to the formation of undesirable by-products. Other known methods require tedious control during manufacture and do not always produce the desired end-product. Still other methods require extensive agitation and/or heat, have a short shelf-life, produce products which are not easily storable except under undesirable temperature conditions, etc. Also, it is extremely desirable that a manufactured concentrate be easily mixed with water at the site of application, rather than having to be shipped or transported therewith. Currently, a variety of expensive materials are required in order to mix the biocide-containing composition before it is usable for its intended purpose.

As a result of these problems, there exists a need for economical, easy to handle concentrates which are storage stable, which are low melting solids or liquids, which are easily and readily prepared in a simple container and can be shipped water-free to the end users, e.g., farmers, who can readily mix them with water prior to spraying them onto the sites of application and preferably which imparts a sustained release effect to the biocide.

OBJECTS OF THE INVENTION

It is an object of this invention to provide liquid or low melting solid concentrates of agricultural chemicals which readily emulsify when mixed with water. It is another object to provide such concentrates which are substantially non-aqueous apart from the normal water contents of the components, i.e., an aqueous phase is present therein, thereby rendering them usefully long term storage stable. It is another object to provide such concentrates which can be prepared without heating and extensive stirring or other manner of agitation. It is still another object to provide such concentrates which can be readily formed into stable aqueous emulsions by farmers and other end-users thereof without the necessity of expensive mixing equipment. It is still another object to provide such concentrates which impart a sustained release effect to the agricultural chemical at the sites of application. Other objects will be apparent to those skilled in the art to which this invention pertains.

SUMMARY OF THE INVENTION

In a composition aspect, this invention relates to a storage stable, water emulsifiable, substantially nonaqueous liquid or low melting solid concentrate adapted for on-site preparation of an aqueous emulsion of an agricultural chemical, consisting essentially of a solution, in (a) a liquid hydrophobic agricultural chemical having biocidal activity, of (b) a solid hydrophobic polymer, in an amount effective to achieve release of (a), and (c) an emulsifying agent in an amount effective to form a stable oil-in-water emulsion when the concentrate is mixed with water.

In a process aspect, this invention relates to a method of preparing an agricultural concentrate which comprises mixing (a) a liquid hydrophobic agricultural chemical having biocidal activity, with (b) amount of a solid hydrophobic polymer in particulate form, effective to achieve a sustained release of the agricultural chemical, and (c) an emulsifying agent in an amount effective to form a stable oil-in-water emulsion when the concentrate is mixed with water, thereby forming a liquid or low melting solid solution of (b) and (c) in (a).

In a method of use aspect, this invention relates to a method of imparting a sustained release effect to an agricultural chemical which comprises the steps of mixing the emulsifiable concentrate consisting essentially of a solution, in (a) a liquid hydrophobic agricultural chemical having biocidal activity, of (b) a solid hydrophobic polymer, in an amount effective to achieve release of (a), and (c) an emulsifying agent in an amount effective to form a stable oil-in-water emulsion when the concentrate is mixed with water, so as to form an oil-in-water emulsion, and applying the resultant emulsion to the locus.

DETAILED DISCUSSION

The solid polymers which are present in the concentrates of this invention are hydrophobic, i.e., water insoluble, polymers which have a low permeability to water. Such polymers effect the sustained release of the active agricultural agent.

The most preferred polymer, polystyrene, has inherent viscosities between about 0.083 dL/g to 0.44 dL/g, preferably about 0.28 dL/g to about 0.34 dL/g. These viscosities are based on the relationship between the weight average molecular weight ($\overline{MW}_w$) and the inherent viscosity ($\eta_{Inh}$) at a concentration of 0.100 g/dL in toluene at 25° C.

$$\overline{MW} = 3.19 \times 10^3 \eta_{Inh} 1.3914$$

Solid polymers which may utilized and methods of preparing them are well known in the art. Examples of polymers may be utilized include poly(methyl methacrylate) and poly(vinyl acetate).

A preferred class of polymers is polystyrene and substituted polystyrenes, e.g., substituted in the aromatic ring by lower-alkyl, e.g., methyl, ethyl, tert.-butyl, tert.-amyl, halo, e.g., fluorine, chlorine or bromine, as well as a variety of combinations, multiples and/or mixtures of these. The most preferred polymer is polystyrene.

The polymers employed in the concentrates of this invention must be soluble in the agricultural chemical therein, e.g., at least 20% by weight and preferably at least 40% by weight at ambient temperatures. They must also be non-reactive with the agricultural chemical, i.e., they must be storage stable as a solution therein for at least 6 months and preferably much longer.

The polymer component ordinarily comprises about 20 to 50 wt %, preferably about 40 to 45 wt %, of the concentrate.

A wide variety of one or more agricultural chemicals having biocidal activity can be employed in the concentrates of this invention, e.g., those having nematocidal, insecticidal, fungicidal or pesticidal activity, provided the agricultural chemical is hydrophobic and liquid at room temperature. Examples of such agricultural chemicals are Fumazone (1,2-dibromo-3-chloropropane), Dowfume W(1,2-dibromoethane) and Telone (1,3-dichloropropene).

The liquid biocide component typically is present in the concentrate at a concentration of about 10 to 50 weight percent, most preferably 35 to 45 weight percent. As stated above, the agricultural chemical is liquid which is a solvent for the other components present in the concentrate.

The oil-in-water emulsifying agent or agents employed in the concentrates of this invention are well-known in the art. Suitable types of emulsifiers are non-ionic surfactants, e.g., Triton® ×-405 (Rhom and Haas), anionic surfactants, e.g., Calsul® HF (Thompson Hayward Chemical Co.), and mixed surfactants, e.g., Atlox® 3409 (ICI Americans, Inc.)

However, in the broadest embodiment, any suitable surface active agent capable of forming stable emulsions of the agricultural chemical-polymer solution may be employed without departing from the spirit and scope of this invention.

Mixtures of the surfactants are preferred, but selection is not sharply critical. Some combinations are better than others. Those skilled in the art can make a selection.

The most preferred emulsifier is a mixture of Triton® ×405 and Casul® 70 HF. It is also suitable to use mixtures of emulsifiers.

These emulsifying agents ordinarily are present in the concentrate at a concentration of about 6 to 12 wt %, most preferably about 8 to 10 wt %.

The concentrates of this invention are produced by forming a liquid or low melting solid solution of the selected solid polymer and emulsifying agent in the liquid agricultural chemical. This can be accomplished by merely allowing an intimate mixture of the three ingredients to stand for several minutes, hours or days. The formation of the solution can be expedited by mild heating and/or stirring.

The polymer and emulsifying agent can be mixed with the agricultural chemical together or sequentially, in either order, although the presence of the emulsifying agent in the agricultural chemical tends to aid in the dissolution of the polymer therein.

Some of the commercially available surfactants contain a small amount of water. Any water in the concentrate greater than about 0.1% can be removed in a separator or with the aid of a solid desiccant like Drierite, which, in turn, can be separated from the concentrate by decantation. These are skills well known to those in the art.

The resulting concentrate of this invention is a liquid or a low melting solid, e.g., melting below 25°, preferably below 20°, and most preferably below 0° C. Above its freezing point it is a liquid solution of the polymer and emulsifying agent in the agricultural chemical.

Because the agricultural chemical is the solvent for the polymer and the emulsifying agent, the concentrates of this invention if the concentrate is a solid at the ambient temperature at which it is to be used, the formation of the emulsion in water is expedited by gentle warming at the site of use, thereby converting it into a liquid, or by first mixing it with a small amount of water and stirring until a pourable mixture is obtained, before mixing it with the final amount of water.

Although the essential ingredients of this invention are the hydrophobic liquid agricultural chemical, the hydrophobic polymer and the emulsifying agent, other conventional anhydrous materials may also be present therein, e.g., a suspending agent, viscosity regulating agents, etc., providing they do not interfere with the function of the three vital components.

In a preferred embodiment, the resulting concentrate is a solution of a liquid agricultural hydrophobic biocide having dissolved therein a solid, hydrophobic polymer and a suitable emulsifying agent, which upon mixing with water, preferably the point of application, forms a stable emulsion, i.e., remains as a single emulsified phase on standing without agitation for at least 30 minutes, preferably at least one hour and more preferably twelve hours or more. The particular polymer and the agricultural chemical used are mutually compatible, with the polymer functioning as a reservoir for the controlled release of the agricultural chemical, e.g., biocide, after dispersing by spraying onto the soil. The resulting concentrate is readily prepared by simply combining the ingredients in a single mixing vessel with agitation, but without heat, e.g., at room temperature. Thus, the concentrate is easily and directly distributed, after packaging, to its end users without the burdensome requirement of other preparation steps; e.g., precipitation of the polymer and biocide with a non-solvent under shearing action, drying, grinding and the like. The resulting concentrate has an extremely long shelf life since water is absent from the formulation, and is easily stored under temperature conditions unsuitable for a water-based emulsion, i.e., the concentrate can be stored below the freezing point of water. At the time and place of application, the formulation is mixed with water using simple mixing equipment typically available to farmers, rather than requiring sophisticated or high-speed, heavy mixing equipment which is common to factories or laboratories. In fact, domestic garden hose sprayers or the like can readily be used and since the emulsion is readily prepared at the place of application, the water ingredient does not have to be shipped or transported, thereby resulting in a much lighter product and a significant economic saving. Upon mixing with water, the biocide-containing concentrate is converted into a water-based emulsion, containing the dispersed polymer phase into which is dissolved the biocide. The emulsion is stabilized by the surfactant, while the water-sensitive biocide is protected from the water phase. The resulting emulsion is then used as a delivery vehicle for applying the biocide to the situs, e.g., growing plants or soil. Evaporation of the water leaves the biocide in its dispersed polymer reservoir, where it is released in a sustained manner to the applied environment, where its biological effects are exerted.

The amount of concentrate which is mixed with water is an amount calculated to deliver 1.0 lbs/acre to 10 lbs/acre of active biocide in about 0.25 gal to about 10 gal or more of emulsion. The preferred volume of emulsion to be delivered per acre is about 0.5 gal to about 5 gal.

The pests such as the nematodes, soil disease and other undesirables, and the like are controlled by applying the particles in any convenient formulation to the locus of infestation, to the area to be protected, or to the pests themselves. Where the control of these tests in agricultural crops is desired, the resulting emulsion is generally applied to the foliage or other plant parts that are infested or which are to be protected or to the locus, at a time depending on the mode of action of the particular active ingredient involved. The precise amount to be applied depends on the particular species to be controlled, its life stage, its size and location, the amount of rainfall, the time of year, moisture, temperature, type of application, and other variables known to those in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLES

Formation of Emulsifiable Polymer Concentrate (EPC)

To 5 g of polystyrene (Dow, PS 2, MW 55,000) in a glass bottle was added 5 g of "Telone II," liquid mixture of equal parts of cis- and trans-1,3-dichloropropenes (95%) and a mixture of other chlorinated propenes and propanes (5%). The bottle was capped and the mixture allowed to stand until the solubilization of the polymer in the Telone II was complete, usually less than 24 hours. To the resulting viscous, pourable solution was added 0.5 g of 70% Triton ® ×-405 (Rohm and Haas, France S.A.) comprising 70% octylphenoxypolyethoxy (HLB 17.9) and 0.5 g of 70% Casul ® 70 HF (Thompson Hayward Chem. Co.), calcium alkylaryl sulfonate (70%)-anionic (HLB 10.5) surfactants producing an EPC of Telone II.

The resulting EPC of Telone II was diluted with 10 g of water, mixed by shaking for about 1 min, and allowed to stand undisturbed for up to 16 hr; the oil-in-water emulsion that had formed initially was still stable.

Following the above procedure, other polystyrene, Telone II and surfactant combinations were prepared and evaluated as EPC's and the data is set forth in Table I below.

TABLE I

Observations on solutions formulating 2 parts (wt) $H_2O$ per 1 part Telone II[a]

| Formulation No. | Polystyrene (MW 55M) (g) | Telone II ® (g) | Surfactant(s) Name | Surfactant(s) (g) | Observations 0.5 hr. | Observations 1. hr. | Observations 16 hr. |
|---|---|---|---|---|---|---|---|
| 1 | 5 | 5 | Tx[b]<br>C[c] | 0.34<br>0.24 | ca Two equal phases | No change | — |
| 2 | 5 | 5 | TX<br>C | 0.25<br>0.25 | SEP[d] | SEP | Two phases, EP phase major, re-dispersible |
| 3 | 5 | 5 | TX<br>C | 0.67<br>0.47 | SEP | SEP | SEP |
| 4 | 5 | 5 | TX<br>C | 0.50<br>0.50 | SEP | SEP | SEP |
| 5 | 5 | 5 | TX<br>C | 0.76<br>0.38 | Two phases | | |
| 6 | 5 | 5 | A[e] | 0.50 | SEP | SEP | Two phases, EP larger |
| 7 | 5 | 5 | A | 1.00 | SEP | SEP | Two phases, slight loss of EP |

TABLE I-continued

Observations on solutions formulating 2 parts (wt) H₂O per 1 part Telone II[a]

| Formulation No. | Polystyrene (MW 55M) (g) | Telone II ® (g) | Surfactant(s) Name | (g) | Observations 0.5 hr. | 1. hr. | 16 hr. |
|---|---|---|---|---|---|---|---|
| 8 | 5 | 5 | G[f] | 0.50 | SEP | SEP | Slight tendency toward polymer agglomeration |
| 9 | 5 | 5 | G | 1.00 | SEP | SEP | Three phases |
| 10 | 5 | 6 | TX C | 0.52 0.26 | Two phases, EP major | Two phases | — |
| 11 | 5 | 6 | TX C | 1.00 0.52 | Two phases, EP major | Slight loss of EP | Two phases, EP larger |
| 12 | 5 | 6 | A | 0.55 | SEP | SEP | Polymer agglomeration |
| 13 | 5 | 6 | A | 1.10 | No EP | No change | Polymer agglomeration |
| 14 | 5 | 6 | G | 0.55 | SEP | Slight phase separation, EP major | Polymer agglomeration |
| 15 | 5 | 6 | G | 1.1 | SEP | SEP | Polymer agglomeration |
| 16 | 5 | 7 | TX C | 0.57 0.29 | Two phases, EP major | No change | Slight loss of EP phase |
| 17 | 5 | 7 | TX C | 1.2 0.62 | Two phases, EP major | Two phases, EP major | Polymer agglomeration |
| 18 | 5 | 7 | A | 0.6 | SEP | Two phases EP major | Polymer agglomeration |
| 19 | 5 | 7 | A | 1.2 | SEP | Two phases EP major | Polymer agglomeration |
| 20 | 5 | 7 | G | 0.6 | Polymer agglomeration | — | — |
| 21 | 5 | 7 | G | 1.2 | SEP | Slight loss of SEP | Polymer agglomeration |

[a]Amount of water = 2X wt. of Telone II
[b]Triton ® X-405, 70%
[c]Casul ® 70 HF, 70%
[d]Single Emulsified Phase
[e]Altox ® 3409
[f]Garfac ® RM-510

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A storage stable, water emulsifiable, substantially non-aqueous liquid or low melting solid concentrate having a water content not greater than about 0.1% which is adapted for use in the on-site preparation of an aqueous emulsion of an agricultural chemical, consisting of a solution of
   (a) at least one liquid hydrophobic agricultural chemical having biocidal activity from the group consisting of 1,2-dibromoethane, 1,3-dichloro-propene and 1,2-dibromo-3-chloropropane,
   (b) a solid hydrophobic polymer, in an amount effective to achieve sustained release from the concentrate of the compound of (a), and
   (c) an emulsifying agent, in an amount effective to form a stable oil-in-water emulsion when the concentrate is mixed with water.

2. A method for the controlled delivery of an agricultural chemical to a locus, comprising
   mixing the emulsifiable concentrate of claim 1 with water so as to form an oil-in-water emulsion; and applying the resulting emulsion to the locus.

3. A concentrate as claimed in claim 1, wherein the concentrate is a liquid at ambient temperature.

4. A concentrate as claimed in claim 3, wherein the agricultural chemical is present in the concentrate at a concentration of about 10 to 50 wt %.

5. A concentrate as claimed in claim 4, wherein the hydrophobic polymer is polystyrene or a substituted polystyrene, or a mixture thereof.

6. A concentrate as claimed in claim 5, wherein the polymer is polystyrene.

7. A concentrate as claimed in claim 6, wherein the polymer is present in the concentrate at a concentration of about 20 to 50 wt %.

8. A concentration as claimed in claim 7, wherein the emulsifying agent is an anionic surfactant.

9. A concentrate according to claim 8, wherein the agricultural chemical is 1,3-dichloropropene.

10. A concentrate according to claim 8 wherein the agricultural chemical is 1,2-dibromoethane.

11. A concentrate according to claim 8 wherein the agricultural chemical is 1,2-dibromo-3-chloropropane.

12. A method of forming a storage stable, water emulsifiable, substantially non-aqueous concentrate which comprises mixing
   (a) at least one liquid hydrophobic agricultural chemical having biocidal activity from the group consisting of 1,2-dibromoethane, 1,3-dichloropropene and 1,2-dibromo-3-chloropropane with
   (b) an amount of a solid hydrophobic polymer in finely divided particulate form, effective to achieve a sustained release of the agricultural chemical and
   (c) an emulsifying agent, in an amount effective to form a stable oil-in-water emulsion when the concentrate is mixed with water thereby forming a liquid or low melting solid solution of (b) and (c) in (a).

* * * * *